United States Patent [19]

Norton

[11] Patent Number: 4,515,593
[45] Date of Patent: May 7, 1985

[54] MEDICAL TUBING HAVING EXTERIOR HYDROPHILIC COATING FOR MICROBIOCIDE ABSORPTION THEREIN AND METHOD FOR USING SAME

[75] Inventor: William J. Norton, Berkeley Heights, N.J.

[73] Assignee: C. R. Bard, Inc., Murray Hill, N.J.

[21] Appl. No.: 336,291

[22] Filed: Dec. 31, 1981

[51] Int. Cl.³ ............................................ A61M 25/00
[52] U.S. Cl. .................................................... 604/265
[58] Field of Search ...................... 604/265, 264, 280; 427/44

[56] References Cited

U.S. PATENT DOCUMENTS

| | | | |
|---|---|---|---|
| 3,566,874 | 3/1971 | Shephard et al. | 427/44 X |
| 3,604,426 | 9/1971 | Erickson | 604/265 |
| 3,695,921 | 10/1972 | Shepard et al. | 427/2 |
| 3,699,956 | 10/1972 | Kitrakis et al. | 604/265 |
| 4,055,688 | 10/1977 | Merrill | 604/103 X |

*Primary Examiner*—Stephen C. Pellegrino
*Attorney, Agent, or Firm*—Dennison, Meserole, Pollack & Scheiner

[57] ABSTRACT

A catheter or the like having a body portion formed of a hydrophobic elastomer and having a predetermined selected portion of the exterior surface, intermediate the ends, coated with a hydrophilic elastomer for reception of a microbiocide along a limited portion at the cite of the entry of the catheter into the body.

8 Claims, 3 Drawing Figures

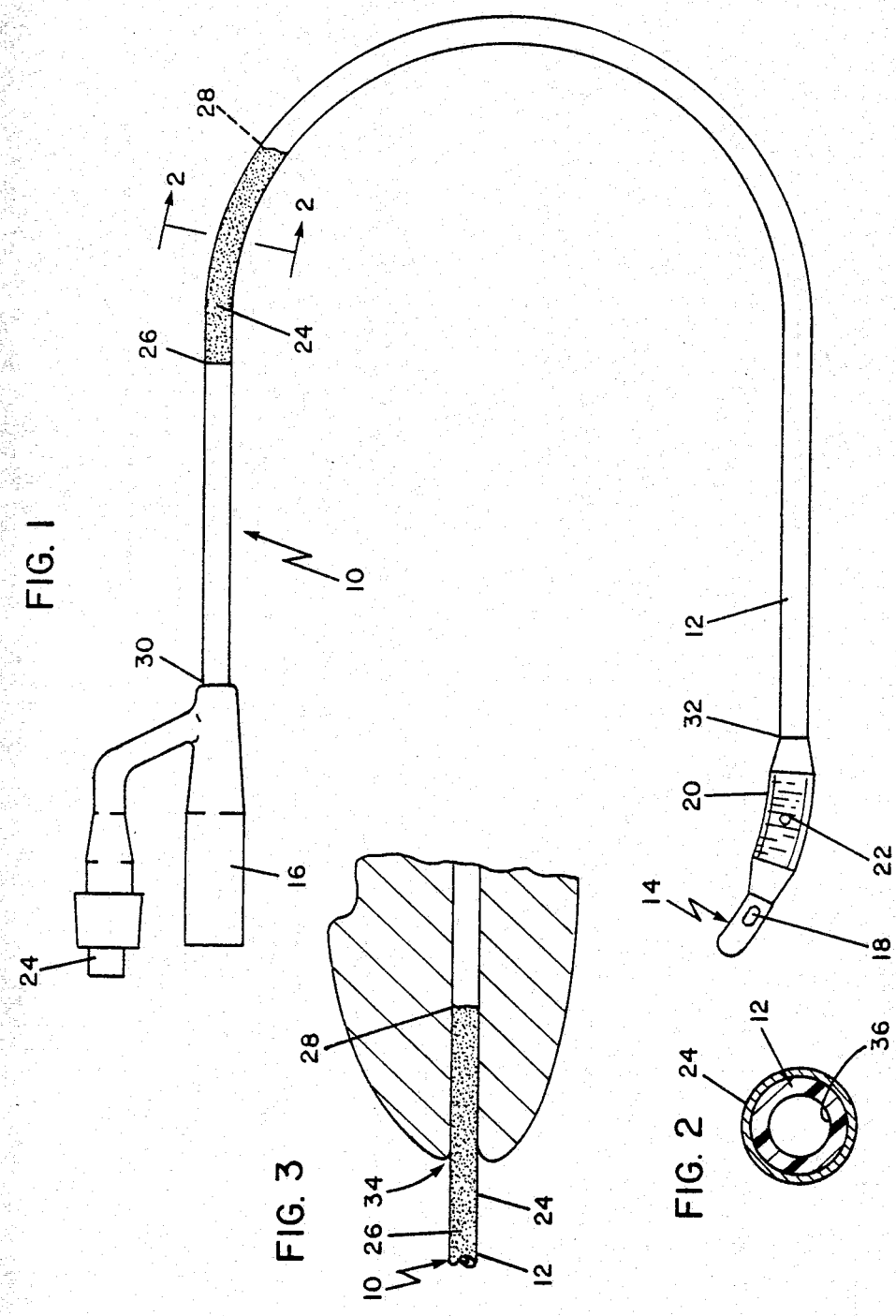

MEDICAL TUBING HAVING EXTERIOR HYDROPHILIC COATING FOR MICROBIOCIDE ABSORPTION THEREIN AND METHOD FOR USING SAME

BACKGROUND OF THE INVENTION

The present invention relates generally to provision of elastomeric tubing having utility for medical devices and particularly urethral and venous catheters. Such catheters normally are considered to be indwelling catheters in that they are placed and retained within the urethra or a vein for an extended period of time. It is well recognized that such catheters oftentimes comprise a principal avenue for introduction of pathogenic organisms.

Probably the biggest problem, and the greatest danger to the patient, that exists when using an indwelling urethral catheter, such as a Foley catheter, is infection that almost always occurs after the catheter has been indwelling for a few days. Clinical studies tend to show that the catheter, both internally and externally provides an avenue for entry of pathogenic organisms. In the former instance with respect to organisms gaining access through the interior of the catheter it is now becoming commonplace to provide means for killing organisms that would otherwise multiply in a urine drainage bag operatively connected to the catheter. In the latter instance attempts have been made to prevent organisms from entering the urethral passage between the wall of the urethra and the exterior surface of the catheter. However, such attempts with respect to providing a barrier that would prevent organisms from entering the urethral passage between the urethra and catheter oftentimes result in introducing additional problems not the least of which is increased irritation, and thus inflamation, of tissue by prior art catheters, which condition it will be appreciated materially enhances the likelihood of infection attendant the use of an indwelling catheter or the like. It will be understood that an indwelling catheter, such as a Foley catheter, is merely exemplary and that the same problems exist with respect to other drainage tubes as well as venous catheters.

Generally, prior art attempts to provide catheters intended to eliminate or minimize infection comprise catheters in which a microbiocide capable of withstanding the conditions attendant the manufacture of the catheter are actually incorporated in a composition comprising a catheter. Such catheters normally achieve a microbiocidal effect by virtue of the fact that in use the microbiocidal agents in the base material bleed to the surface and in the case of a urethral catheter result in irritation of the wall of the urethra and it is believed that catheters with such a construction are no longer in use.

A subsequent generation of indwelling catheters resorted to a somewhat different approach in an attempt to reduce infection. In this regard, and since the tubular body portion of most catheters is formed of a natural or synthetic elastomer that is hydrophobic, prior art catheters such as formed of silicone rubber have had substantially their entire surfaces, both interior and exterior, coated with a hydrophilic polymer to enable the absorbtion of aqueous solutions or suspensions of microbiocides, including antibiotics, into the coating.

In this regard U.S. Pat. No. 4,055,682 to Merrill is directed to a catheter having a silicone body portion rendered hydrophilic by contacting it with N-vinyl pyrrolidone (NVP) and exposing the catheter and NVP to ionizing radiation. U.S. Pat. Nos. 3,566,874 and 3,695,921 to Shepherd et al are representative of indwelling Foley urethral catheters made of natural or synthetic rubber and having an external coating of a hydrophylic acrylate or methacrylate polymer grafted thereto for the stated purpose of reducing irritation and infection and wherein it is indicated that the hydrophilic polymer may be impregnated with an antibiotic or germicide.

It has been found that there are severe problems encountered by both the systems of Merrill and Shepherd et al in that if a microbiocide is applied to substantially the entire surface of a catheter, in use, it will cause irritation and probably do more damage to the patient than if a standard untreated catheter were used. Further, if an antibiotic is impregnated into the surface of a catheter then only those organisms that are rendered dormant or killed by that particular antibiotic would be effected whereby the protective flora would be damaged with a possibility that other organisms normally subdued by the flora would run rampant and thus the use of an antiobiotic impregnated catheter would tend to induce rather than prevent infection.

Even more significantly it should be noted that rendering a surface of a catheter hydrophilic causes other problems. One of the most significant problems in this regard is brought about by the very nature of the coating, its hydrophilicity, that provides a wettable surface. Thus, once such wettable surface is in contact with a physiological fluid such as urine, for example, which has dissolved salts and other solid compounds in its composition, the hydrophilic coating by virtue of uptake of the aqueous moiety of such physiological fluid provides a nucleus for the accretion of salt due to a supersaturated condition adjacent the coating as well as accretion of other solid components of the composition. An unfortunate end result is a plugged catheter or a catheter with a sharp accretion of salts and the like on the exterior surface of the catheter. Needless to say in the instance of an urethral catheter having such an accretion on the exterior thereof the removal of the catheter brings about a situation not unlike the passing of a jagged kidney stone through the urethra.

SUMMARY AND OBJECTS OF THE INVENTION

The present invention provides a catheter structure and method of use that substantially overcomes the problems attendant prior art hydrophilic polymer coated indwelling catheters.

The invention contemplates rendering only a segment of the surface of a hydrophobic catheter hydrophilic such as by the application of a coating as exemplified by the referenced patents to Merrill and Shepherd et al.

The disclosure of U.S. Pat. No. 4,055,682 to Merrill is hereby incorporated by reference with respect to catheters having a body formed of hydrophobic elastomer having a hydrophilic coating grafted thereto by coating the catheter with NVP and subjecting the coated catheter to ionizing radiation.

The disclosures of U.S. Pat. Nos. 3,566,874 and 3,695,921 to Shepherd et al are hereby incorporated by reference with respect to the provision of hydrophilic acrylate and methacrylate coatings on otherwise hydrophobic catheters.

The object of invention comprising minimizing irritation and infection attendant the use of an indwelling catheter is achieved by providing only a segment of the catheter surface hydrophilic, which segment is generally the portion of the catheter generally external to the body whereby a microbiocidal agent is only contained in that segement of the catheter that is generally external to the body.

Another object of the invention comprising minimizing accretion of salts and the like on and within, the catheter is achieved by coating only the exterior surface of a generally hydrophobic catheter with a hydrophilic polymer and preferably only coating that portion of the catheter that will, in use, be contiguous with and exteriorly disposed relative to the urinary tract meatus or other opening through which the catheter enters the body.

Still another object to the invention comprises a method of minimizing irritation and infection attendant the use of an indwelling catheter and facilitating removal of the catheter by providing only a segment of the cathether surface hydrophilic, introducing the catheter into a body orifice or the like and concurrent therewith swabbing the hydrophilic segment with an aqueous solution or dispersion of a microbiocide such as povidone iodine and completing placement of a catheter with only a minimal portion of the microbiocide-containing hydrophilic coating within the body.

Still another object of the invention comprising minimizing irritation and infection attendant the use of an indwelling catheter is achieved by providing only a segment of the cather surface hydrophilic, which segment is generally a portion of the catheter generally external to the body, which coated segment at the point of use has applied thereto by the physician, physician's assistant, nurse, etc. an aqueous solution or dispersion of a microbiocide such as povidone iodine.

Various other objects and advantages of the invention will be readily apparent from the following detailed description taken in conjunction with the drawings in which an exemplary embodiment of the invention is shown.

DESCRIPTION OF THE DRAWINGS

FIG. 1 is a perspective view of an urethral catheter embodying the invention;

FIG. 2 is an enlarged cross-section of the body portion of the catheter taken along the lines 2—2 of FIG. 1; and FIG. 3 is a fragmentary side elevational view of the body portion of the catheter in FIG. 1 showing the manner of its placement relative to the urinary tract meatus of a male patient.

DESCRIPTION OF THE PREFERRED EMBODIMENT

Referring more specifically to FIGS. 1 and 2 of the drawings there is provided an improved constant drainage indwelling Foley urethral catheter 10 such as formed of silicone rubber. The catheter 10 includes a tubular portion 12 terminating in a tip portion indicated generally at 14. The catheter body 10 includes a drainage lumen, not shown, that connects a funnel 16 with a drainage port 18. An inflatable retaining bag or balloon 20 encompasses the tube 12, at a point inwardly of drainage port 18, and is sealed or otherwise connected thereto in conventional fashion. A longitudinally extending inflation lumen, not shown, terminates in an inflation port 22 which communicates the interior of the balloon 20 with a valve end portion or arm 24 for the introduction of water to inflate the balloon 20 to retain the catheter tip 14 in the bladder.

The body portion 12 is formed of a relatively flexible elastomer, e.g., silicone rubber, which is hydrophobic and generally inert with respect to physiological fluids it contacts. The body portion 12 of the catheter 10 is selectively coated on the exterior surface with a hydrophilic polymeric coating 24 such as formed from NVP or an acrylate or methacrylate monomer as set forth in the incorporated Merrill and Shepherd et al patents. It will be understood that hydrophilic polymers formed from NVP or acrylate or methacrylate monomers are merely exemplary and that other hydrophilic monomers are satisfactory as long as they are physiologically compatable and are capable of absorbing, and/or adsorbing, a solution or dispersion of a conventional microbiocide such as povidone iodine.

In the exemplary embodiment 10 illustrated the hydrophilic coating 24 is grafted to the exterior of the body portion 12 over only a minor longitudinal portion, or segment, of the body portion 12 between the points 26 and 28, which extent of the coating 24 is predetermined so as to be positioned and be of a sufficient extent for use in conjunction with a male patient. In this regard, and with specific reference to FIG. 3, the catheter 10 is shown operatively positioned within the urethral tract of a male patient with the portion thereof provided with the exterior hydrophilic coating 24 generally contiguous with the meatus 34 and wherein the extremities 26 and 28 of the coating 24 "straddle" the meatus 34. The stippling, or shading of the coating 24 is indicative of the application thereto of povidone iodine, or the like, preferably at the time of placement of the catheter so as to ensure only a minor portion of the inner wall of the uretha, or other body tissue, is subjected to the microbiocide and to also ensure that at least a portion of the microbiocide impregnated catheter extends exteriorly of the meatus or other body opening.

It will be appreciated that it is also consonant with the present invention that the coating 24 with povidone iodine, or the like, impregnated therein be provided at the time of manufacture of the catheter and the coated microbiocide impregnated catheter packed under aseptic conditions or packaged and sterilized by suitable means, for subsequent use. In such instance it will be appreciated that using an accepted technique the catheter would be removed from its sterile package and the tip portion 14 passed upwardly through the urethra for placement of the catheter as illustrated in FIG. 3.

Still further, it will be appreciated that the invention contemplates grafting, or otherwise coating, the body portion 12 of the catheter 10 with a hydrophilic coating on a substantially longer segment of the catheter, e.g., between the point 30 adjacent the funnel 16 and the point 32 at the base of the balloon 20, it being understood that such coating is provided only on the outside of the catheter. In use the catheter provided with an hydrophilic coating extending between points 30 and 32 would be inserted into the body and a longitudinally extending portion of the catheter swabbed with a suitable conventional microbiocide, such as povidone iodine, along a segment "straddling" the meatus or other body opening.

This latter mode of carrying forth the invention merely obviates the necessity for predetermining the positioning and extent of the coating, as with the coating portion 24, thereby ensuring that the catheter is of general utility, i.e. adaptable for use with a female patient as well as a male patient. This latter approach is of course preferred where it is necessary to minimize the number of items stocked by a clinic or hospital.

It is significant to note that irrespective of the longitudinal extent of the hydrophilic coating on the catheter 10, e.g., extending between points 26 and 28 or points 30 and 32, such coating is restricted to the exterior of the body portion 12 and does not include comparable coating of the wall 36 defining the drainage lumen, as best seen in FIG. 2. Accordingly encrustation and/or plugging of the drainage lumen is obviated. Furthermore the selective minimal longitudinal extent of the application of the microbiocide to the hydrophilic coating greatly minimizes the contact of microbiocide with body tissue thereby greatly minimizing the irritation of body tissue it being appreciated of course that to some degree or another virtually all microbiocides comprise tissue irritants. Nonetheless the present invention enables a significant reduction in the irritation, and attendant infection that generally ensues, from excessive exposure to microbiocide used in conjuntion with indwelling catheters and the like. Further, the predetermined highly selective localized hydrophilic coating of the catheter minimizes the contact of the catheter with physiological fluids as would lead to encrustation and the problems attendant thereto.

It will be apparent that other variations may be perceived by those skilled iu the art without departing from the scope of my invention as defined in the appended claims.

I claim:

1. A catheter for indwelling introduction into a body opening and comprising an elongated relatively flexible body portion formed of a hydrophobic polymer and normally having a hydrophobic exterior surface and including a hydrophilic coating on a predetermined longitudinally extending portion of the exterior surface only of the body portion intermediate the ends thereof, a portion of said hydrophilic coating defining an aqueous-base microbiocide absorption zone which absorption zone will in use straddle an opening through which the catheter enters the body with only a minor portion of the hydrophilic coating indwelling for preventing entry of pathogenic organisms at the in use site of the body opening through which the catheter passes, and said hydrophilic coating within the body only being coextensive with a minor portion of the catheter that is subjected in use to physiological fluid-dissolved compounds wherein in use indwelling incrustation of the catheter is generally obviated.

2. The catheter of claim 1 wherein said hydrophilic coating is in the order of about 0.0005 inches in thickness.

3. The catheter of claim 1 wherein said hydrophilic coating comprises a polymeric coating formed from monomer selected from the group comprising N-vinyl pyrrolidone, acrylate and methacrylate.

4. The catheter of claim 1 comprising a Foley catheter.

5. The catheter of claim 1 comprising a drainage catheter.

6. The catheter of claim 1 comprising a venous catheter.

7. A catheter for indwelling introduction into a body opening comprising an elongated relatively flexible body portion formed of a hydrophobic polymer and normally having a hydrophobic exterior surface and including a hydrophilic coating on the exterior surface of the catheter intermediate the ends thereof, a minor indwelling portion of which coating will straddle an opening through which the catheter enters the body, and a microbiocide absorbed in said coating and extending inwardly only a relatively short distance of an in use site of passage of the catheter into a body opening for preventing entry of pathogenic organisms through the body opening, said hydrophilic coating not being coextensive with hydrophobic body portions that are subjected in use to physiological fluid-dissolved compounds wherein in use encrustation of the catheter is generally obviated whereby withdrawal of the indwelling catheter is facilitated.

8. A method of minimizing irritation of body tissue and likelihood of infection due to an indwelling catheter and facilitating withdrawal of the catheter which method comprises the steps of: providing a catheter having an elongated relatively flexible body portion formed of a hydrophobic polymer with a hydrophilic coating on the exterior surface of the catheter intermediate the ends thereof with only a selected minor indwelling segment of the exterior surface being coated; said hydrophilic coating not being coextensive with hydrophobic body portions that are subjected in use to physiological fluid-dissolved compounds wherein in use encrustation of the catheter is generally obviated whereby withdrawal of the catheter after prolonged indwelling is facilitated, placing the catheter into the body of a patient through an opening; and absorbing an aqueous-base microbiocide into said coating only adjacent a site of entry of the catheter into the patients body wherein said minor segment straddles said site of entry whereby entry of pathogenic organisms through the body opening is prevented.

* * * * *